United States Patent

Wang et al.

Patent Number: 5,512,051
Date of Patent: Apr. 30, 1996

[54] SLIP-LAYERED CATHETER BALLOON

[75] Inventors: James C. Wang, Norton; Yem Chin, Burlington, both of Mass.

[73] Assignee: Boston Scientific Corporation, Natick, Mass.

[21] Appl. No.: 493,088

[22] Filed: Jun. 21, 1995

Related U.S. Application Data

[63] Continuation of Ser. No. 174,680, Dec. 28, 1993, abandoned, which is a continuation-in-part of Ser. No. 17,763, Feb. 16, 1993, abandoned, and Ser. No. 82,594, Jun. 25, 1993, abandoned.

[51] Int. Cl.⁶ .................................................. A61M 29/00
[52] U.S. Cl. .................................................. 604/96; 606/192
[58] Field of Search ............................ 604/96–103, 265; 606/192–194; 600/18; 264/171–172, 174

[56] References Cited

U.S. PATENT DOCUMENTS

| | | | |
|---|---|---|---|
| 2,499,045 | 2/1950 | Walker et al. | 604/96 |
| 4,417,576 | 11/1983 | Baran | 604/101 |
| 4,423,725 | 1/1984 | Baran et al. | 604/101 |
| 4,572,186 | 2/1986 | Gould et al. | 606/194 |
| 4,637,396 | 1/1987 | Cook | 606/194 |
| 4,702,252 | 10/1987 | Brooks et al. | 606/195 |
| 4,896,669 | 1/1990 | Bhate et al. | 606/194 |
| 4,994,047 | 2/1991 | Walker et al. | 604/265 |
| 4,994,072 | 2/1991 | Bhate et al. | 606/194 |
| 5,061,254 | 10/1991 | Karakelle et al. | 604/265 |
| 5,108,416 | 4/1992 | Ryan et al. | 606/194 |
| 5,201,706 | 4/1993 | Noguchi et al. | 604/96 |
| 5,213,576 | 5/1993 | Abiuso et al. | 604/96 |
| 5,232,444 | 8/1993 | Just et al. | 604/96 |
| 5,330,429 | 7/1994 | Noguchi et al. | 604/96 |

FOREIGN PATENT DOCUMENTS

| | | | |
|---|---|---|---|
| 0467516 | 1/1992 | European Pat. Off. | 606/194 |
| 1069826 | 9/1982 | U.S.S.R. | 604/21 |

*Primary Examiner*—C. Fred Rosenbaum
*Assistant Examiner*—Mark Bockelman
*Attorney, Agent, or Firm*—Frances P. Craig

[57] ABSTRACT

A slip-layered balloon catheter for insertion into a bodily conduit, especially an artery. The catheter comprises a shaft (21) having at least one lumen (26) for delivery of a fluid inflation media and a slip-layered balloon (12) made up of a plurality of layers with a low-friction substance between the layers. The low-friction substance causes the layers to slide readily relative to one another, softening the balloon while maintaining its strength. Optionally, the balloon includes a plurality of slip-layered segments radially disposed about the balloon wall, and separated by lengthwise ridges joining the layers of each segment together. Also optionally, an elastic sleeve surrounds the balloon wall to improve refoldability of the balloon.

15 Claims, 2 Drawing Sheets

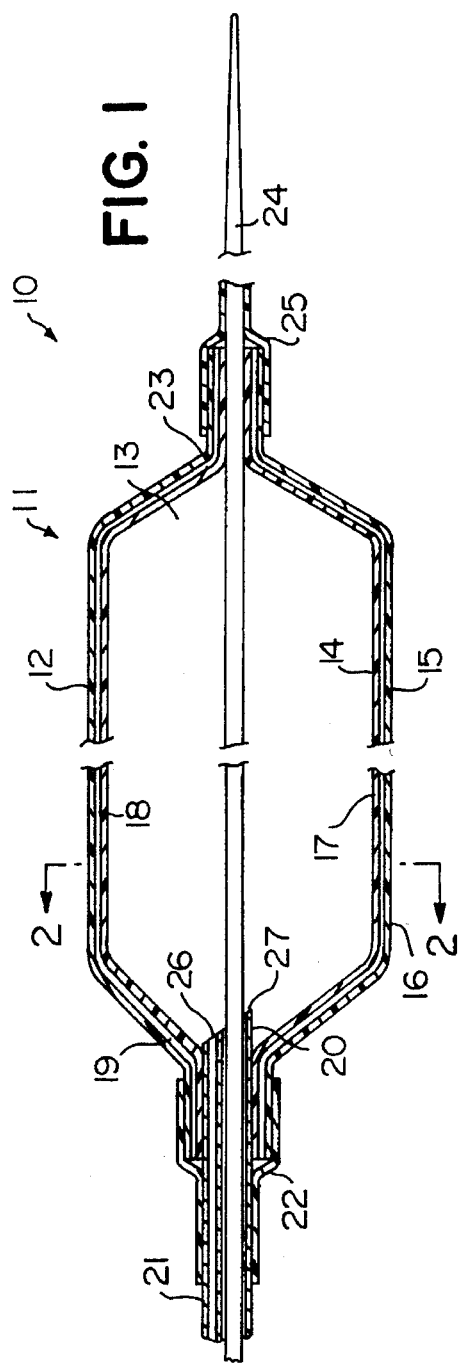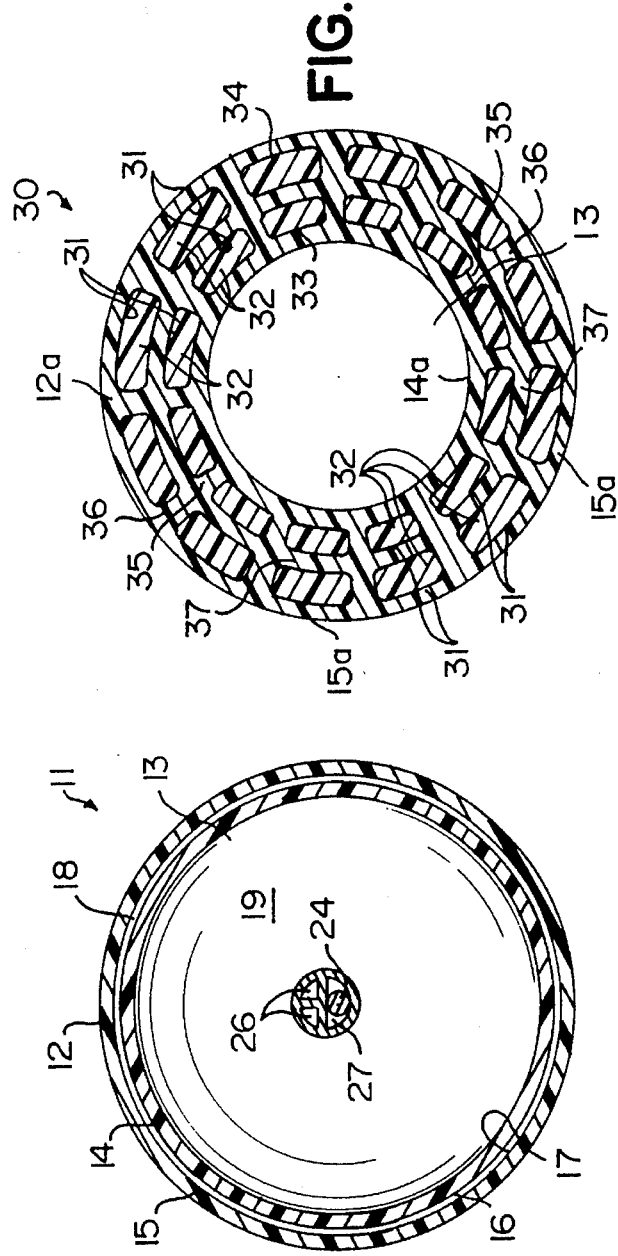

SLIP-LAYERED CATHETER BALLOON

CROSS REFERENCE TO RELATED APPLICATIONS

This is a continuation of application Ser. No. 08/174,680 filed on Dec. 28, 1993 now abandoned which is a continuation-in-part of commonly assigned, U.S. patent applications Ser. Nos. 08/017,763, filed Feb. 16, 1993 now abandonded by J. Wang, and 08/082,594, filed Jun. 25, 1993 now abandonded by J. E. Abele et al. Applications 08/017,763 and 08/082,594 are hereby incorporated herein by reference.

BACKGROUND OF THE INVENTION

The present invention relates to balloons for medical catheter applications, wherein a catheter with a balloon at the proximal end is positioned within a bodily conduit and inflated to expand the conduit, and to methods of fabrication of such balloons.

Typical balloon catheters have a balloon fastened around the exterior of a hollow catheter tube or shaft, with the balloon in fluid flow relation with the interior of the shaft. The shaft provides a fluid supply for inflating the balloon.

Examples of such balloon catheters are catheters for prostate therapy, TTS endoscopic catheters for gastrointestinal use, and PTA and PTCA catheters for angioplasty. For example, coronary angioplasty can involve the insertion of a PTCA (percutaneous transluminal coronary angioplasty) catheter through a patient's artery to an arterial stenosis, and injecting a suitable fluid into the balloon to inflate it. The inflation expands the stenosis radially outwardly and compresses it against the artery wall to increase the cross-sectional area of the artery so that the artery has an acceptable blood flow rate.

Some known catheter balloons are fabricated from non-compliant materials such as polyethylene terephthalate (PET) or Nylon. Non-compliant balloons present the advantages of high burst strength and predetermined maximum diameter. These balloons can prevent damage to tissues due to over-inflation, since they do not increase in diameter significantly beyond the point of full inflation. Their disadvantages, however, include stiffness and poor foldability. Further, on deflation these balloons can present sharp edges and corners which can cause trauma to bodily tissues as the catheters are withdrawn.

Other known balloons are fabricated from compliant materials such as polyethylene (PE) or ethylene vinyl acetate (EVA). The diameter of these balloons is dependent on the pressure of the inflation fluid. The compliant balloons are easily folded, and are softer than the non-compliant balloon, thus are less likely to cause trauma during their passage through the body. However, the variable diameter of the non-compliant balloons must be carefully monitored to prevent tissue damage and catastrophic failure of the balloon during inflation. They can also present the disadvantages of lower tensile strength than the non-compliant balloons. Increasing the wall thickness to offset the lower tensile strength can present an undesirably large profile in the folded balloon.

It would be desirable to have a medical catheter balloon which combines the best properties of the compliant and non-compliant balloons, with low compliance, high burst strength, low folded profile, softness, and pliability. The invention described herein was developed to address that need.

SUMMARY OF THE INVENTION

In a first aspect, the invention is a slip-layered balloon for use with a medical catheter device. The balloon includes a wall defining a chamber, the wall including at least two layers of a polymeric medical balloon material. Between the layers is a low-friction substance imparting a low coefficient of friction between facing surfaces of the layers, so that the layers become slip-layers which readily slide with respect to one another as the balloon is inflated and deflated. A typical configuration for the balloon wall is a generally cylindrical central portion between tapered proximal and distal end portions.

In a narrower aspect, the balloon wall is unitary, with layers joined to one another at a plurality of ridges, each extending the length of the wall. Each ridge is separated from other ridges by slip-layered segments in which the layers become slip-layers which readily slide with respect to one another as the balloon is inflated and deflated.

In another narrower aspect, the balloon further includes an elastic sleeve surrounding and coextensive with the wall. The low-friction substance in such a sleeved balloon can also be disposed between the elastic sleeve and the outermost layer, so that a low coefficient of friction is imparted between facing surfaces of the elastic sleeve and the outermost layer and such that the elastic sleeve and the outermost layer also become slip-layers which readily slide with respect to one another as the balloon is inflated and deflated.

In another aspect, the invention is a catheter for insertion into a bodily conduit. The catheter includes a shaft with a lumen for delivery of fluid inflation media, a balloon having a wall concentric with the shaft and defining a chamber. The chamber is in fluid communication with the lumen for inflation of the balloon. The balloon wall includes at least two non-adhering layers of a polymeric medical balloon material. Between the layers is a low-friction substance imparting a low coefficient of friction between facing surfaces of the layers, so that the layers become slip-layers which readily slide with respect to one another as the balloon is inflated and deflated.

In yet another aspect, the invention is a method for fabricating a slip-layered balloon for use with a medical catheter device. The method involves providing on a first layer of a medical balloon material at least one additional layer to form a balloon wall including at least two layers of a medical balloon material. The wall defines a chamber. A low-friction substance is disposed between said layers imparting a low coefficient of friction between facing surfaces of the layers, so that the layers become slip-layers which readily slide with respect to one another as the balloon is inflated and deflated.

In a narrower aspect of this method, the additional layer on said first layer is provided by extruding the medical balloon material to form the first layer and the additional layer of the balloon wall. In a preferred method, a polymeric medical balloon material and a second polymeric material are coextruded so that the medical balloon material forms a continuous phase providing a generally tubular balloon blank and the second material forms a discrete phase. The discrete phase is surrounded by the continuous phase and provides strands extending lengthwise within the blank. The strands are then removed from the blank and the strand-removed blank is shaped to form a balloon including a unitary wall defining a chamber. The balloon wall includes at least two layers of a the medical balloon material joined to one another at a plurality of ridges, each of the ridges extending the length of the wall and being separated from other ridges by layered segments of the wall. A low-friction substance is disposed between the layers of the segments, imparting a low coefficient of friction between facing surfaces of the layers, so that the layers become slip-layers which readily slide with respect to one another as the balloon is inflated and deflated. In a most preferred method, the second material is softer than the medical balloon material, and the strands are removed by scoring the balloon blank to form a score-line in the circumferential direction along the outermost surface of the medical balloon material near an end of the blank, without affecting the second material. The medical balloon material is then broken at the score-line to separate the medical balloon material of the end of the blank from the remainder of the medical balloon material. The separated medical balloon material is removed from the blank by pulling the separated medical balloon material off of the strands, thereby exposing an end of each strand. The strand ends are then gripped and pulled to remove the strands from the blank.

BRIEF DESCRIPTION OF THE DRAWINGS

FIG. 1 is a cross-sectional view of a balloon catheter in an inflated condition in accordance with one embodiment of the present invention.

FIG. 2 is a cross-sectional view of the balloon shown in FIG. 1, taken along the line 2—2.

FIG. 3 is a cross-sectional view of a coextruded balloon blank for fabricating a balloon in accordance with an alternate embodiment of the present invention.

DETAILED DESCRIPTION OF THE PREFERRED EMBODIMENTS

Figure 4:
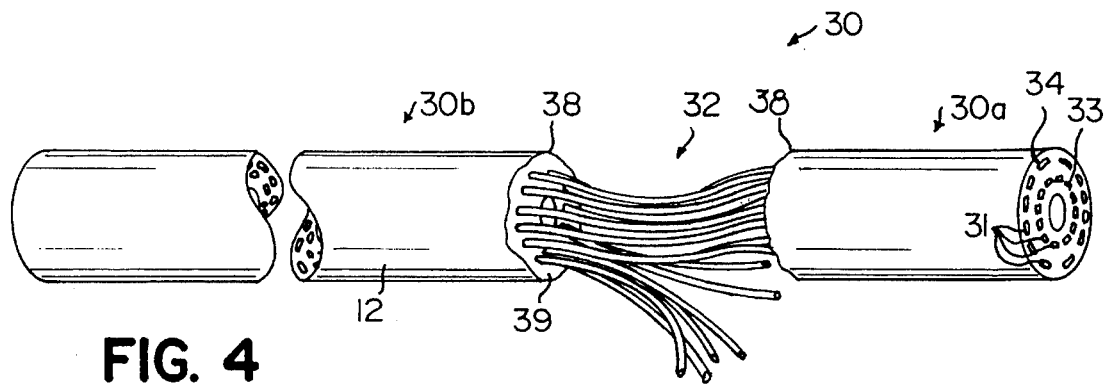
FIG. 4 is an elevation view of the balloon blank of FIG. 3, illustrating the withdrawal of the second phase strands to leave open channels in the balloon blank.

An exemplary embodiment of the balloon in accordance with the invention utilizes a non-compliant balloon in which the balloon wall encloses a chamber. The balloon has two or more concentric thin layers of high strength medical balloon material, with provision made to overcome the normally occurring high coefficient of friction existing between the interfacial surfaces of the balloon layers. That is, a sufficiently low coefficient of friction between the layers exists for the layers to be very slippery against each other. The number of layers in the balloon wall typically is 2 to about 10 layers, preferably 3–5 layers, with provision made for a low coefficient of friction between adjacent pairs of layers.

This slip-layered balloon deforms easily, since little force is necessary to cause the layers to slide against (move relative to) one another. This sliding movement is principally in the circumferential direction, and may be likened to the sliding against one another of the pages of a paperback booklet when the booklet is bent into a curve. Although the booklet may be the same thickness as a similar sized piece of paperboard, it is softer and more flexible. Similarly, even if each individual layer is stiff and strong, the slip-layered balloon described herein feels soft and pliable, and folds down easily. This improvement in properties is achieved even in a balloon having a total thickness greater than is normally used for a particular medical purpose.

The balloon layers may be fabricated from any high strength material known to be suitable for medical balloons, and preferably from a non-compliant material. Examples of preferred non-compliant materials suitable for fabrication of the balloon are polyethylene terephthalate (PET), most preferably biaxially oriented PET, Nylon, polypropylene (PP), and other non-compliant engineering resins known to be suitable for medical balloon applications. Suitable compliant materials are polyethylene (PE), particularly biaxially oriented PE (irradiated), polyvinyl chloride (PVC), and other compliant polymers known to be suitable for medical balloons.

The low coefficient of friction between layers may be provided by coating the interfacial surfaces of the balloon layers with a low-friction substance, or otherwise inserting a low-friction substance between the layers. Examples of such a low-friction substance include silicone, silicone oil, fluorocarbons, and other lubricants known to be suitable for medical uses. The softness, pliability, and foldability of such a slip-layered balloon is significantly greater than that of a single layer balloon of the same total thickness, and even than that of a multi-layered balloon of the same total thickness without the low-friction substance between the layers.

The coextensive layers of the slip-layered balloon described herein may be fabricated by separately forming (e.g., by extrusion) tubular balloon blanks, either formed with or stretched to progressively larger diameters, and sliding progressively larger tubes over the smaller tubes to assemble the individual layers into a multi-layered balloon blank. If necessary, the larger tubes may be shrink-fitted over the smaller diameter tubes. In a preferred alternative, however, the layers are extruded simultaneously (coextruded) to form the balloon blank. If desired, the innermost and/or outermost layers of a multi-layered balloon may be thicker than the intermediate layer(s) for improved abrasion resistance. The balloon blank may then be shaped by conventional means to form the balloon. In one exemplary shaping process, the blank is heated and inflated to form, e.g., a cylindrical balloon body with tapered portions between the body and the balloon proximal and distal ends. As part of such a shaping process, the blank may be stretched to orient the material and/or to form thinner layers and/or ends.

The low-friction substance may be coated on or otherwise inserted between the layers by any one of several means. For example, separately fabricated layers may be coated with the low-friction substance, e.g., by dipping, wiping, or spraying with the substance alone or in solution before assembling the layers to form the balloon blank. Alternatively, the assembled or commonly extruded layers of the blank may be coated, e.g., by soaking the blank in a solution of the substance or by forcing the substance or its solution between the layers under pressure. One example of a suitable solution of a low friction substance is a solution of about 2%–10% silicone oil in Freon. The blank may then be shaped by conventional methods to form a medical balloon for use with a catheter. Preferably, the low friction substance is applied before shaping to prevent adhering of the layers together during the shaping process. Most preferably, the low-friction material is applied both before and after shaping.

A catheter utilizing the herein-described slip-layered balloon may be similar to any conventional balloon catheter assembly, with the herein-described novel balloon substituted for the conventional balloon. The catheter includes a shaft, and the proximal end of the slip-layered balloon typically is joined to the shaft at the shaft distal end. The length of the catheter is sufficient to be threaded through the bodily cavity or cavities to the area to be treated with a sufficient length remaining outside the body to permit manipulation of the catheter. The shaft includes at least one internal lumen for inflating the balloon with a fluid inflation medium. Typically, a guidewire extends through the balloon, and may extend distally from the balloon. Alternatively, a wire may extend proximally through the shaft (via an additional lumen) to provide greater stiffness and strength to the shaft.

The catheter may be fabricated by conventional means, except for the fabrication of the novel slip-layered balloon, described above, and the joining of the balloon to the catheter at the balloon's proximal and distal ends. The proximal joint may be accomplished by adhering the layers to one another at the balloon ends and adhering the innermost layer to the shaft. Alternatively, the layers may be trimmed to overlap one another and successively adhered to the shaft, or only the innermost and outermost layers may be adhered. Heat sealing and/or adhesive are suitable for this joining process. An improved seal may be achieved by adhering the innermost layer to the shaft, slipping a flexible polymeric sleeve cover over the shaft with its distal end overlapping the balloon end, then adhering the sleeve cover to both the outermost layer and the shaft. Similar joining methods may be used to anchor the proximal end of the balloon to, e.g., the guidewire. Optionally, the outer surface of the balloon or the entire catheter may be further coated with a conventional slip coating, for example silicone or a hydrophilic coating, to ease passage of the catheter through the body.

In a particularly preferred embodiment of the slip-layered balloon, a unitary balloon wall is fabricated in which regions of slip-layered wall extend lengthwise between "ridges", i.e. long, narrow regions in which the layers of the balloon are joined to one another through the thickness of the balloon, the joined regions normally visible as ridges or stripes on the outside surface of the balloon wall. The unitary nature of the ridged slip-layered balloon provides better quality control and simplifies joining of the balloon ends to the catheter, since the layers are already fixed to one another at the ridges.

The ridged design also results in differential stiffness about the circumference of the balloon, encouraging regular, multiple-fold collapse of the balloon during deflation and ensuring a smaller diameter for the collapsed balloon. On deflation, multiple folds form in a regular pattern about the circumference of the balloon wall as the balloon wall collapses. The regular fold pattern, in turn, provides a smaller collapsed profile than is usual with the prior art balloons, especially the stiffer non-compliant balloons. This smaller profile can ease passage of the deflated balloon through the arteries during withdrawal of the catheter.

The ridged slip-layered balloon may be fabricated by heat-sealing or otherwise joining together the separate layers of the above described multi-layered balloons along the ridges, leaving layered segments between the ridges. (Preferably, each heat-sealed ridge is continuous along the length of the balloon.) However, the preferred method of fabricating such a ridged slip-layered balloon is to extrude a balloon blank with open channels extending lengthwise through the wall of the blank to divide regions of the wall into multi-layered segments. For example, the wall of a blank for a ridged two-layered balloon is fabricated with a single cylindrical array of a plurality of radially disposed, axially extending channels within the thickness of the wall. The channels are separated by ridges formed by the non-channeled portions of the wall. After shaping of the balloon from the blank, the channels effectively divide the single balloon wall into inner and outer walls in the regions between the ridges. The channels and ridges may extend in a straight line parallel to the balloon axis, or they may be "wrapped" in a helical pattern about the balloon axis.

A balloon with more than two layers in the layered segments between ridges is similarly fabricated, except that at least one additional array of channels is formed, each array at a different radial position within the wall of the balloon blank. The channels of each array preferably are superimposed over one another to provide multi-layered segments sharing a common ridge between each pair of adjacent segments. The surfaces enclosing each channel are coated with the low-friction substance described above to provide a slip-layered balloon, but with the advantages of unitary construction, as described below.

In a most preferred method, a blank for the ridged slip-layered balloon is fabricated by coextruding a hollow tube of two or more dissimilar polymeric materials using conventional extrusion techniques. A discrete phase, that is a phase which serves as the precursor of the channels (and which dictates their location and shape) is formed of, for example, high density polyethylene, Nylon, low density polyethylene, or polyethylene copolymers. A continuous phase, that is the phase that will form the balloon blank with the discrete phase enclosed within the walls thereof, can be formed of polyethylene terephthalate or high or low density polyethylene. High density polyethylene, low density polyethylene and polyethylene copolymers can be extruded within polyethylene terephthalate. Nylon can be extruded within a high or low density polyethylene. Typically, the material of the continuous phase is harder and more brittle than the softer, more pliable discrete phase material. Normally, the strands of all arrays are formed of the same second-phase material. However, arrays of different strand materials as well as strands of different materials in the same array are within the scope of the invention.

After the phases are coextruded, the discrete phase is withdrawn from the continuous phase to leave open channels internal to the continuous phase, as described above. Coextrusion of two polymeric materials is well known, and conventional techniques are used for this process. Criteria for matching of two polymeric materials for the above-described coextrusion are that they not adhere to each other after extrusion and that the discrete phase can be withdrawn from the continuous phase leaving channels therein.

In one method for removing the strands from the coextruded balloon blank, the material of the continuous phase of the balloon blank is harder and more brittle than that of the discrete phase strands. A notch is scratched into the outer surface of the blank, extending in a circumferential direction. (The notch need not extend about the entire circumference of the balloon wall.) The blank then can be fractured cross-sectionally by exerting tensile stress at the notch (for example, by bending the balloon blank) without breaking the strands, and the fractured continuous phase is separated from the blank.

The discrete phase strands then can be withdrawn from the continuous phase, forming a tubular balloon blank of, e.g., polyethylene terephthalate with a plurality of open channels within its wall. The shape, number, and arrangement of the channels can be varied as desired by the operator by varying the design of the extrusion die. For example, the strands described above may be round, ovoid, square, rectangular, etc. in cross-section. Also, any number of arrays between 1 and about 10, preferably about 3–7, is possible through the total thickness of the balloon, n–1 arrays producing n layers in each shaped, ridged, slip-layered balloon. Any number of channels in each array between 1 and about 24 is possible, preferably about 3–10. Normally, the ridges are of a circumferential width smaller than that of the slip-layered segments.

The open channel balloon blank is then shaped by conventional means, e.g. heating and inflation, to form a ridged balloon. During the shaping process, the chamber enclosed by the inner surface of the heated balloon is inflated, but the channels within the wall itself are not pressurized. Thus, the layers formed by the inner and outer walls of the channels are stretched to a greater extent than the walls joining the channels in each array, creating a plurality of layered wall segments separated by ridges. If desired, the innermost and/or outermost layers may be thicker than any intermediate layers present, providing increased toughness and strength. The channels are coated with silicone oil or other low-friction substance such that the layered segments are slip-layered segments which readily slide relative to one another, as described above. This ridged balloon is a strong, soft medical balloon in which ridges and slip-layered segments provide differential stiffness about the circumference of the balloon for improved foldability. Additionally, the ridges anchor the layers to one another providing easier joining of the balloon to the catheter.

While coextrusion is generally the preferred method for forming the ridged balloons, it is also possible to extrude tubes having the channels already formed therein using a known type of extrusion die. However, the thickness of the channels within the blank is extremely small, typically about 0.025–0.5 mm within a tubular balloon blank having a total wall thickness between about 0.07 and 1.0 mm and outside diameter between about 0.25 and 5.0 mm. Therefore, extrusion with the desired preformed channels can be more difficult than coextrusion, and coextrusion is generally preferred.

The foldability and surface characteristics of any of the balloons described herein, and particularly of the ridged balloons, may be improved by providing an elastomeric or elastic sleeve surrounding the balloon wall. The sleeve may be fabricated of such materials as silicone rubber, polyurethane elastomer, polyamide elastomer, polyolefin elastomer, thermoplastic elastomers (e.g., an engineering thermoplastic elastomer), or any elastomer considered suitable for use in medical catheters.

The elastic sleeve is of a size, thickness, and elastic modulus such that it fits closely around the slip-layered balloon wall in its completely deflated or collapsed state, expands with the balloon wall as the balloon is inflated to its maximum diameter, and contracts as the pressure in the balloon is decreased during deflation, collapsing the sliplayered balloon wall into a tight, compact, generally cylindrical bundle. A typical thickness for the elastic sleeve is about 0.003"–0.020". To further encourage the collapse of the balloon wall, as well as to permit more even expansion of the elastic sleeve, a coating of silicone oil or other low-friction substance may be disposed between the slip-layered balloon wall and the elastic sleeve. The elastic sleeve and low-friction coating cooperate with the slip layers, and in the ridged balloon with the ridges to refold the balloon in, e.g., a helical wrap about the axis of the balloon. Ridges in the sleeved balloon assure that the folding will occur along predetermined lines along the length of the balloon. The sleeve is fabricated, applied to the balloon, and joined to the catheter by known means.

Referring now to FIGS. 1 and 2, catheter 10, not drawn to scale, includes slip-layered balloon 11, shown in its inflated state, in which slip-layered balloon wall 12 encloses chamber 13. Balloon wall 12 includes inner layer 14 and outer layer 15. Layers 14 and 15 are coextensive, and are disposed with interfacial surfaces 16 and 17, respectively, facing one another. Surface 16 and/or surface 17 are coated with silicone oil 18, and layer 15 is heat treated to shrink-fit layer 15 over inflated layer 14 such that no air bubbles are enclosed between surfaces 16 and 17. Thus, silicone oil coating 18 causes layers 14 and 15 to slide with respect to one another, such that slip-layered balloon 11 is softer and more pliable than prior art balloons. In FIGS. 1 and 2, balloon wall 12 is shown with two layers with a silicone oil coating between the two layers. Alternatively, balloon wall may have up to about 10 layers, with silicone oil or other low-friction substance between facing surfaces of the layers.

Balloon 11 is shown in FIG. 1 with its proximal end 19 fixed to distal end 20 of shaft 21 by sleeve cover 22 and adhesive (not shown). Balloon distal end 23 is fixed to wire 24 in a similar manner by sleeve cover 25. Balloon chamber 13 is in communication via lumens 26 with a source (not shown) of an inflation medium for inflation of balloon 11. In the embodiment of FIG. 1, wire 24 extends proximally through balloon chamber 13 and through lumen 27 of catheter 10.

Inflation of chamber 13 causes balloon wall 12 to expand from a folded arrangement around wire 24 to being spaced therefrom. This expansion causes proximal and distal ends 19 and 23 to assume generally conical shapes and allow for an increase in the diameter of balloon 11 and for pressing of balloon wall 12 against the lesion being addressed.

A typical balloon diameter when the balloon chamber is fully inflated is about 0.04–2 in. The thickness of each of layers 14 and 15 typically is about 0.0001–0.004 in, with 0.0003–0.002 in being preferred. The deflated profile of balloon 11 typically is about 0.03–0.25 in.

FIGS. 3 and 4 illustrate coextruded balloon blank 30, from which an alternate embodiment of the balloon described herein is fabricated. In FIGS. 3 and 4, like features to lo those shown in FIGS. 1 and 2 are indicated by the same reference numerals.

In FIG. 3, balloon blank 30 has continuous phase balloon wall 12a of non-compliant polyethylene terephthalate balloon material. Balloon wall 12a includes channels 31 filled by discrete phase strands 32 of a high density polyethylene. Channels 31 are disposed in inner and outer cylindrical arrays 33 and 34, respectively, around an axis, not shown, which can be similar to wire 24. Each of channels 31 share a common "connector" wall, wall 35 or 36, with the next adjacent of channels 31 in array 35 or 36, respectively. Thus, in this embodiment, innermost layer 14a, outermost layer 15a, and intermediate layer 37 are each present as segments joined by connector walls 35 and 36.

After coextrusion, strands 32 are removed from balloon blank 30 by withdrawing the strands from channels 31, as illustrated in FIG. 4. A notch or groove (not shown) is scratched into the outer surface of continuous phase balloon wall 12a at 38, the notch extending in a short circumferential arc about the balloon wall. The hard, brittle continuous phase balloon wall 12a is fractured cross-sectionally by bending the balloon blank to exert tensile stress at the notch. The soft, pliable strands remain unbroken during this process. The fractured continuous phase 12a may then be separated into portions 30a and 30b. Shorter portion 30a is pulled away from longer portion 30b, permitting part of each strand 32 to be withdrawn from channels 31 in shorter portion 30a, and to extend from cross-sectional surface 39 of longer portion 30b. The exposed parts of strands 32 are then gripped and pulled, withdrawing strands 32 from channels 31 in longer portion 30b to form a balloon blank with open channels. The open channels of the balloon blank are then coated with, e.g., silicone oil, as described above, and the balloon blank is shaped by conventional means, e.g. heating and inflation, to form a ridged balloon, described in more detail below.

The coextruded balloon blank of FIGS. 3 and 4, as mentioned above, is fabricated from two dissimilar materials, the harder, more brittle polyethylene terephthalate continuous phase forming the balloon wall and the softer, more pliable high density polyethylene discrete phase forming the removable strands. However, other dissimilar material combinations may be used, as described above.

Figure 5:
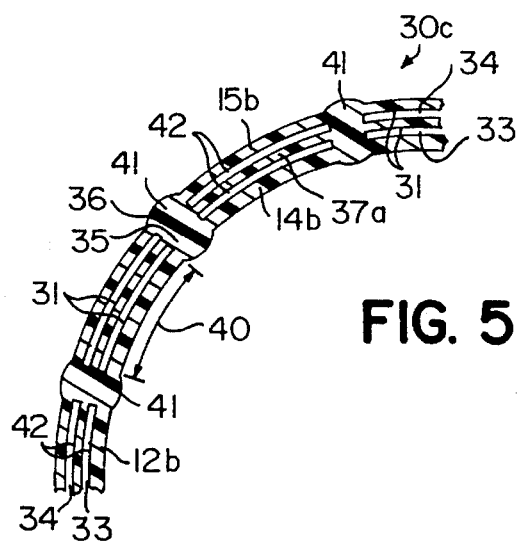
FIG. 5 is a cross-sectional view of a portion of the balloon fabricated from the balloon blank of FIGS. 3 and 4.

As the discrete phase is withdrawn from the continuous phase, a tubular balloon blank is formed having a plurality of open channels within its wall. For the balloon blank of FIGS. 3 and 4, the discrete phase is extruded such that the channels within the shaped balloon are disposed to define two cylindrical arrays, as shown in FIG. 5. The shape and arrangement of the channels can be varied as desired by the operator by varying the design of the extrusion die.

FIG. 5 illustrates in cross-section a portion of ridged balloon 30c. In FIG. 5, like features to those shown in FIGS. 1–4 are indicated by the same reference numerals. Balloon 30c is fabricated from coextruded balloon blank portion 30b of FIG. 4 (after withdrawal of strands 32 from channels 31) by heating and inflation of balloon blank portion 30b, in a conventional manner, to form a balloon similar in shape to balloon 11 of FIG. 1. (The cross-section shown in FIG. 5 is taken at a position on the balloon similar to cross-section 2—2 of FIG. 1.) During the shaping process, layers 14a, 37, and 15a of balloon wall 12a (FIG. 3) are stretched to a greater extent than connecting walls 35 and 36 (FIG. 3), creating a plurality of layered wall segments 40 (of shaped balloon wall 12b) separated by ridges 41. Each layered segment 40 is made up of innermost thin balloon wall layer 14b, outermost thin balloon wall layer 15b, and intermediate thin balloon wall layer 37a. In the embodiment shown in FIG. 5, intermediate layer 37a is thinner than either of layers 14b and 15b. Layers 14b and 37a and layers 37a and 15b are separated by channels 31, which have been coated with silicone oil 42 such that segments 40 are slip-layered segments which readily slide relative to one another, as described above. Thus, balloon 30c is a strong, soft, ridged medical balloon in which ridges 41 and slip-layered segments 40 provide differential stiffness about the circumference of the balloon for improved foldability. Additionally, ridges 41 anchor the layers to one another providing easier joining of the balloon to the catheter.

Figure 6:
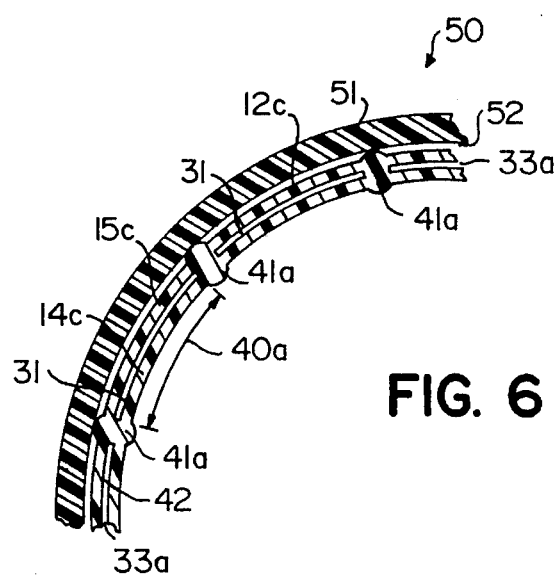
FIG. 6 is a cross-sectional view of a portion of a balloon in accordance with another alternate embodiment of the present invention.

FIG. 6 illustrates in cross-section a portion of yet another embodiment of the balloon described herein. In FIG. 6, like features to those shown in FIGS. 1–5 are indicated by the same reference numerals.

Ridged balloon 50 of FIG. 6 includes non-compliant balloon wall 12c made up of slip-layered segments 40a separated by ridges 41. Segments 40a include channels 31 arranged in single cylindrical array 33a. Channels 31 separate inner layer 14c and outer layer 15c, and are coated with silicone oil 42 as described above. Surrounding balloon wall 12c is elastomeric sleeve or elastic sleeve 51, fabricated of silicone rubber. Elastic sleeve 51 is of a size, thickness, and elastic modulus such that it fits closely around slip-layered balloon wall 12c in its completely deflated or collapsed state, expands with balloon wall 12c as balloon 50 is inflated to its maximum diameter, and contracts as the pressure in balloon 50 is decreased during deflation, collapsing slip-layered balloon wall 12c into a tight, compact, generally cylindrical bundle. To further encourage the collapse of balloon wall 12c, as well as to permit more even expansion of elastic sleeve 51, coating 52 of silicone oil or other low-friction substance is disposed between sleeve 51 and balloon wall 12c. Elastic sleeve 51 and silicone oil coating 52 cooperate with slip layered segments 40a and ridges 41 to refold balloon 50 in a helical wrap about its axis.

Balloon wall 12c is fabricated by a process similar to that described above for balloon wall 12b. Elastic sleeve 51 may be applied to balloon wall 12c by, for example, prefabricating tubular elastic sleeve 51 by known means, e.g., extrusion, then swelling sleeve 51 by immersing in, e.g., Freon. Prefabricated balloon wall 12c may then be inserted into the enlarged sleeve, and the Freon evaporated to shrink sleeve 51 about balloon wall 12c.

Elastic sleeve 51 is shown in FIG. 6 surrounding a ridged, non-compliant balloon wall having a single array of channels filled with a low-friction substance. However, a similar elastic sleeve may be utilized as part of any compliant or non-compliant slip-layered balloon embodiment in accordance with the present invention. The elastic sleeve of FIG. 6 is described as silicone rubber. Other suitable materials for the sleeve are polyurethane elastomer, polyamide elastomer, polyolefin elastomer, thermoplastic elastomers (e.g., an engineering thermoplastic elastomer), or any elastomer considered suitable for use in medical catheters, as described above.

The slip-layered balloons described herein and the catheters made therefrom present many advantages over those of the prior art. For example, the balloons can combine small folded profiles, high burst pressures, and, optionally, low compliance with improved foldability, pliability, and softness, and high tensile strength. In particular, the ridged slip-layered balloon presents the advantages of fabrication by simple, commercially viable techniques, further improved foldability, and easier joining without significantly sacrificing softness and pliability. Also, the addition of the elastic sleeve described herein even further improves foldability and minimizes folded profile while eliminating sharp folded edges and adding considerable abrasion resistance to the balloon.

It is apparent that modifications and changes can be made within the spirit and scope of the present invention. It is our intention, however, only to be limited by the scope of the appended claims.

We claim:

1. A soft, pliable, inflatable and refoldable slip-layered balloon for use with a medical catheter device, said balloon comprising a wall defining a chamber, said wall comprising at least two imperforate coextensive layers of a non-compliant polymeric medical balloon material, said layers having therebetween a low-friction substance imparting a low coefficient of friction between facing surfaces of said layers, such that said layers become slip-layers which readily slide with respect to one another as said balloon is inflated and deflated.

2. A balloon in accordance with claim 1 wherein said balloon wall comprises at least three layers of said medical balloon material having therebetween said low-friction substance.

3. A balloon in accordance with claim 1 wherein said low-friction substance comprises silicone.

4. A balloon in accordance with claim 1 wherein said balloon wall comprises a generally cylindrical central portion between tapered proximal and distal end portions.

5. A balloon-in accordance with claim 1 wherein said balloon wall is unitary, said layers being joined to one another at a plurality of ridges, each of said ridges extending the full axial length of said wall and being separated from others of said ridges by slip-layered segments extending the full axial length of said wall and in which said layers become slip-layers which readily slide with respect to one another as said balloon is inflated and deflated.

6. A balloon in accordance with claim 1 further comprising an elastomeric sleeve surrounding and coextensive with said wall to aid in refolding said balloon as said balloon is deflated.

7. A balloon in accordance with claim 6 further comprising, between said elastomer sleeve and the outermost of said layers, said low-friction substance, such that a low coefficient of friction is imparted between facing surfaces of said elastomer sleeve and said outermost layer and such that said elastomer sleeve and said outermost layer also become slip-layers which readily slide with respect to one another as said balloon is inflated and deflated.

8. A balloon in accordance with claim 1 wherein said balloon has a fully inflated diameter of about 0.04–2 inches, a deflated, folded profile diameter of about 0.03–0.25 inches, and a layer thickness of about 0.0001–0.004 inches.

9. A soft, pliable, inflatable and refoldable slip-layered balloon for use with a medical catheter device, said balloon comprising a unitary wall defining a chamber, said wall comprising at least two imperforate coextensive layers of a non-compliant polymeric medical balloon material joined to one another at a plurality of ridges, each of said ridges extending the full axial length of said wall and being separated from others of said ridges by slip-layered segments extending the full axial length of said wall and in which said layers have therebetween a low-friction substance imparting a low coefficient of friction between facing surfaces of said layers, such that said layers become slip-layers which readily slide with respect to one another as said balloon is inflated and deflated.

10. A balloon in accordance with claim 9 further comprising an elastomer sleeve surrounding and coextensive with said wall, and further comprising, between said elastomer sleeve and the outermost of said layers, said low-friction substance, such that a low coefficient of friction is imparted between facing surfaces of said elastomer sleeve and said outermost layer and such that said elastomer sleeve and said outermost layer also become slip-layers which readily slide with respect to one another as said balloon is inflated and deflated.

11. A catheter for insertion into a bodily conduit, said catheter comprising:

a shaft comprising a lumen for delivery of fluid inflation media, a soft, pliable, inflatable and refoldable balloon having a wall concentric with said shaft and defining a chamber, said chamber being in fluid communication with said lumen for inflation of said balloon, wherein said wall comprises at least two imperforate coextensive non-adhering layers of a non-compliant polymeric medical balloon material, said layers having therebetween a low-friction substance imparting a low coefficient of friction between facing surfaces of said layers, such that said layers become slip-layers which readily slide with respect to one another as said balloon is inflated and deflated.

12. A method for fabricating a soft, pliable, inflatable and refoldable slip-layered balloon for use with a medical catheter device, said method comprising the steps of:

providing on a first imperforate layer of a non-compliant medical balloon material at least one imperforate coextensive additional layer to form a balloon wall comprising at least two layers of a non-compliant medical balloon material, said wall defining a chamber;

disposing between said layers a low-friction substance imparting a low coefficient of friction between facing surfaces of said layers, such that said layers become slip-layers which readily slide with respect to one another as said balloon is inflated and deflated.

13. A method in accordance with claim 12 wherein said step of providing said at least one additional layer on said first layer comprises extruding said medical balloon material to form said first layer and said at least one additional layer of said balloon wall.

14. A method for fabricating a slip-layered balloon for use with a medical catheter device, said method comprising the steps of:

coextruding a polymeric medical balloon material and a second polymeric material such that said medical balloon material forms a continuous phase providing a generally tubular balloon blank and said second material forms a discrete phase surrounded by said continuous phase and providing strands extending lengthwise within said blank;

removing said strands from said blank;

shaping said strand-removed blank to form a balloon comprising a unitary wall defining a chamber, said wall comprising at least two layers of a said medical balloon material joined to one another at a plurality of ridges, each of said ridges extending the length of said wall and being separated from others of said ridges by layered segments of said wall; and disposing between said layers of said segments a low-friction substance imparting a low coefficient of friction between facing surfaces of said layers, such that said layers become slip-layers which readily slide with respect to one another as said balloon is inflated and deflated.

15. A method in accordance with claim 14 wherein said second material is softer than said medical balloon material, and wherein said strand removing step comprises:

scoring said balloon blank to form a score-line in the circumferential direction along the outermost surface of said medical balloon material near an end of said blank, without affecting said second material;

breaking said medical balloon material at said score-line to separate said medical balloon material of said end from the remainder of said medical balloon material;

removing said separated medical balloon material from said blank by pulling said separated medical balloon material off of said strands, thereby exposing an end of each of said strands; and gripping and pulling on said strand ends to remove said strands from said blank.

* * * * *